US006242598B1

(12) United States Patent
Stevenson et al.

(10) Patent No.: US 6,242,598 B1
(45) Date of Patent: Jun. 5, 2001

(54) METHODS FOR THE PREPARATION OF TRIS-ARYL-O-HYDROXYPHENYL-S-TRIAZINES

(75) Inventors: Tyler Arthur Stevenson, Teaneck, NJ (US); Michael Ackerman, New City, NY (US); Pascal Hayoz, Marly (CH); Roger Meuwly, Cournillens (CH); John Francis Oswald, Woelflinswil (CH); Christian Schregenberger, Olsberg (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/532,222

(22) Filed: Mar. 22, 2000

Related U.S. Application Data

(62) Division of application No. 09/033,266, filed on Mar. 2, 1998, now abandoned.

(51) Int. Cl.[7] ................ C07D 251/22; C07D 251/28
(52) U.S. Cl. .............................. 544/216; 544/219
(58) Field of Search ..................... 544/216, 219

(56) References Cited

U.S. PATENT DOCUMENTS

| | | | |
|---|---|---|---|
| 3,118,887 | * 1/1964 | Hardy | 260/248 |
| 3,244,708 | 4/1966 | Duennenberger et al. | 544/216 |
| 3,293,247 | 12/1966 | Duennenberger et al. | 544/216 |
| 3,397,205 | 8/1968 | Luethi et al. | 544/216 |
| 5,084,570 | 1/1992 | Burdeska et al. | 544/216 |
| 5,106,972 | 4/1992 | Burdeska et al. | 544/216 |

FOREIGN PATENT DOCUMENTS 165608    12/1985  (EP) .
959263    3/1997   (JP) .

OTHER PUBLICATIONS

WeygaNd/Hilgetag., Prep. Org. Chem., Wiley Publication., p. 934, Line 15, 1972.*
Loudon., Organic Chemistry., Addison–Wesley Publishing Co, 1984.*
S. Tanimoto et al., Senryo to Yakuhim 1995, 40(12), pp. 325–339.
H. Brunetti et al., Helv. Chim. Acta., 1972, 55(5), pp. 1566–1595.
E. M. Smolin et al, s–Triazines and Derivatives in the Chemistry of Heterocyclic Compounds, etc. 1959.
Patent Abstracts of Japan 9059263, 1997.
Abstract for EP 165608., 1985.

* cited by examiner

Primary Examiner—Richard L. Raymond
Assistant Examiner—Venkataraman Balasubramanian
(74) Attorney, Agent, or Firm—Tyler A. Stevenson

(57) ABSTRACT

A process for preparing 2-(2,4-dihydroxyphenyl)-4.6-diaryl-s-triazines in three steps starting with cyanuric chloride is described. Step 1 involves the nucleophilic (basic) displacement of one chlorine atom with a phenolic moiety. Step 2 involves a Friedel-Crafts reaction using a Lewis acid catalyst (preferably aluminum chloride) to replace the remaining two chlorine atoms with aryl groups such as xylyl. Finally, step 3 involves replacing the phenolic moiety with resorcinol using either a Lewis acid or protic acid catalyst or combinations thereof. Some additional processes only peripherally related to the three-step process outlined above are also described for the preparation of various s-triazine compounds. The s-triazines prepared are useful as UV absorbers for the stabilization of organic substrates against the adverse effects of actinic light.

38 Claims, No Drawings

METHODS FOR THE PREPARATION OF TRIS-ARYL-O-HYDROXYPHENYL-S-TRIAZINES

This is a divisional of application Ser. No. 09/033,266, filed Mar. 2, 1998, now abandoned.

This invention pertains to novel methods for the preparation of tris-aryl-o-hydroxy-phenyl-s-triazines using cyanuric chloride as a starting material. Particular o-hydroxyphenyl-s-triazines which can be made by these new methods are: bis-aryl-resorcinol based s-triazines; mono-aryl-bis-resorcinol based s-triazines; and tris-resorcinol-s-triazines.

BACKGROUND OF THE INVENTION

Tris-aryl-o-hydroxyphenyl-s-triazines are intermediates for or are themselves UV absorbers useful for the protection of natural or synthetic materials from the adverse action of actinic radiation. There are many methods described for the preparation of such s-triazines as seen from the publications of S. Tanimoto and M. Yamagata, Senryo to Yakuhim, 1995, 40(12), 325–339 and of H. Brunetti and G. E. Luethi, Helv. Chim. Acta, 1972, 55(5), 1566–1595.

The most versatile method is to employ one or more Friedel-Crafts reactions starting from cyanuric chloride. A major obstacle in this approach is the fact that Friedel-Crafts reactions of aryl groups and cyanuric chloride are non-selective. This is a problem when the goal is to prepare an asymmetric tris-aryl-s-triazine. This is explained in the Tanimoto and Brunetti publications mentioned above and in U.S. Pat. Nos. 5,084,570 and 5,106,972. However, it is well-known that substitution reactions between nucleophiles and cyanuric chloride are selective as taught by E. M. Smolin and L. Rapoport, s-Triazines and Derivatives in The Chemistry of Heterocyclic Compounds, A. Weissberger Ed., Interscience Publishers, New York, 1959, pp. 53–57.

One possible approach to prepare asymmetric tris-aryl-s-triazines selectively would be to (a) replace one or two chlorine atoms of cyanuric chloride with an appropriate protecting group in a nucleophilic manner, (b) replace the remaining chlorine atom(s) with the desired aryl group via a Friedel-Crafts reaction; (c) displace the protecting group(s) with chlorine, and finally (d) replace the newly formed chlorine(s) with the second aryl group in a Friedel-Crafts manner. U.S. Pat. Nos. 5,084,570 and 5,106,972 disclose this strategy for the preparation of 2,(2,4-dihydroxyphenyl)-4,6-diaryl-s-triazine. The protecting group chosen in these two patents is methyl mercaptan. The process outlined is four steps starting from cyanuric chloride.

Another drawback of Friedel-Crafts reactions of aryl groups and cyanuric chloride in addition of non-selectivity is the fact that large amounts of Lewis acid are necessary to mediate the reaction, normally equimolar amounts. The Lewis acid most commonly used is aluminum chloride. These reactions produce prodigious amounts of aluminum waste which is environmentally hard to handle.

Japanese Hei 9-59263 discloses a three-step synthetic approach for the preparation of asymmetric tris-aryl-hydroxyphenyl-s-triazines. The preferred method of the Japanese reference is a one-pot process using a Lewis acid to mediate all three steps. This reference will be discussed in more detail later in this application.

A welcome addition to the art therefore would be to (a) provide a method of performing Friedel-Crafts reactions between aryl groups and s-triazines using protic acids instead of Lewis acids, and to (b) provide a method of preparing asymmetric tris-aryl-s-triazines in less than four synthetic steps.

OBJECTS OF THE INVENTION

One object of the invention is a process in which protic acids may be employed as Friedel-Crafts catalysts for the reaction between aryl groups and s-triazines.

Another object of the invention is a method for the preparation of asymmetric tris-aryl-s-triazines in less than four synthetic steps.

A third object of the invention is a process combining the two processes mentioned above.

DETAILED DESCRIPTION OF THE INVENTION

Strong protic acids, such as hydrogen chloride, sulfuric acid, methanesulfonic acid, p-toluenesulfonic acid as well as solid-supported protic acids such as AMBERLYST® (Rohm & Haas), AMBERLITE® (Rohm & Haas) and NAFION® (duPont) catalysts, may be employed as effective Friedel-Crafts catalysts to form carbon-carbon bonds between aryl groups and s-triazines. Active leaving groups are halogen, alkoxy and aryloxy. Preferred leaving groups are chlorine, phenoxy and substituted phenoxy moieties.

The simplest example of a reaction of this type is replacing the chlorine atoms on cyanuric chloride with resorcinol to prepare a tris-2,4,6-(2,4-dihydroxyphenyl)-s-triazine. U.S. Pat. Nos. 3,118,887 and 3.244.708 describe such syntheses, but where large amounts of aluminum chloride are used. Indeed, no added catalyst at all is required as the hydrogen chloride gas released during the initial nucleophilic reaction between resorcinol and cyanuric chloride serves as the catalyst for the carbon-carbon bond formation as seen below:

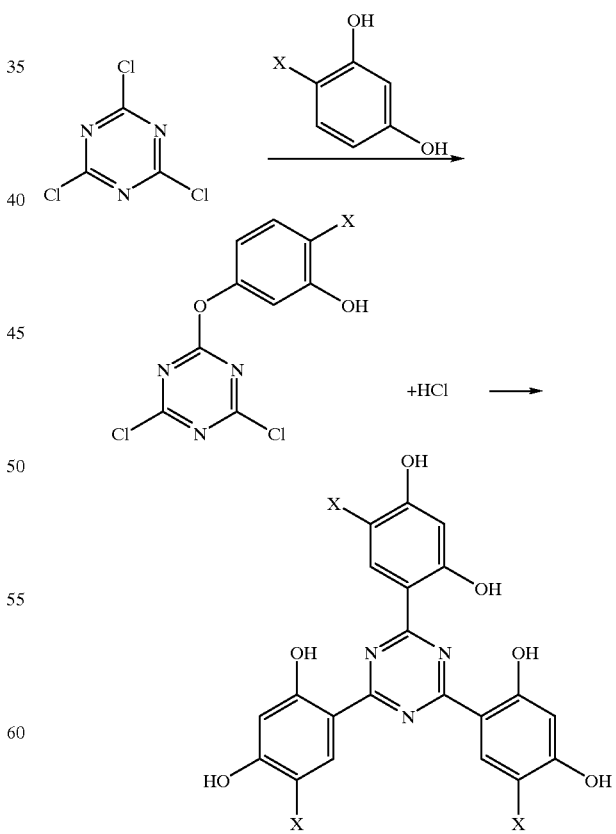

X in these formulae is hydrogen, alkyl, phenylalkyl or halogen.

This reaction may be performed in a solvent or it may be done in neat molten resorcinol. A wide variety of solvents may be used, for example, non-polar hydrocarbons such as xylene or polar solvents such as tetramethylene sulfone. The reaction will work over a wide temperature range from −30° C. to 250° C. An effective temperature range is from 70° C. to 200° C. The most effective temperature range is 100° C. to 170° C.

This reaction may also be performed on mono-aryl-bis-chloro-s-triazines and bis-aryl-mono-chloro-s-triazines as seen below.

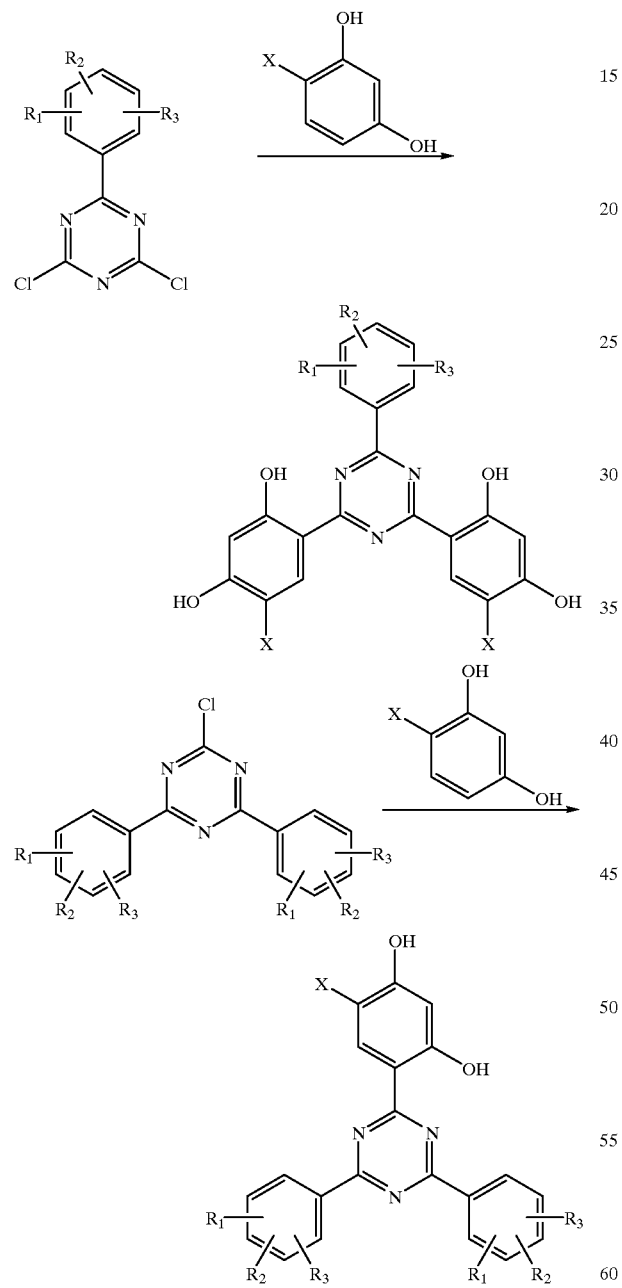

$R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen. The solvents and temperature ranges are those given supra. O-Attached resorcinol groups on the s-triazine ring are observed as transient intermediates during the course of these reactions.

Similar Friedel-Crafts reactions may also be employed with alkoxy or aryloxy moieties as the leaving group. In these cases an external protic acid is added to the mixture. The most effective protic acids are hydrogen chloride gas and methanesulfonic acid. As with halogen, one or more alkoxy or aryloxy groups may be replaced in this fashion. Phenoxy and/or substituted phenoxy groups are especially suitable leaving groups as seen in the reactions outlined below.

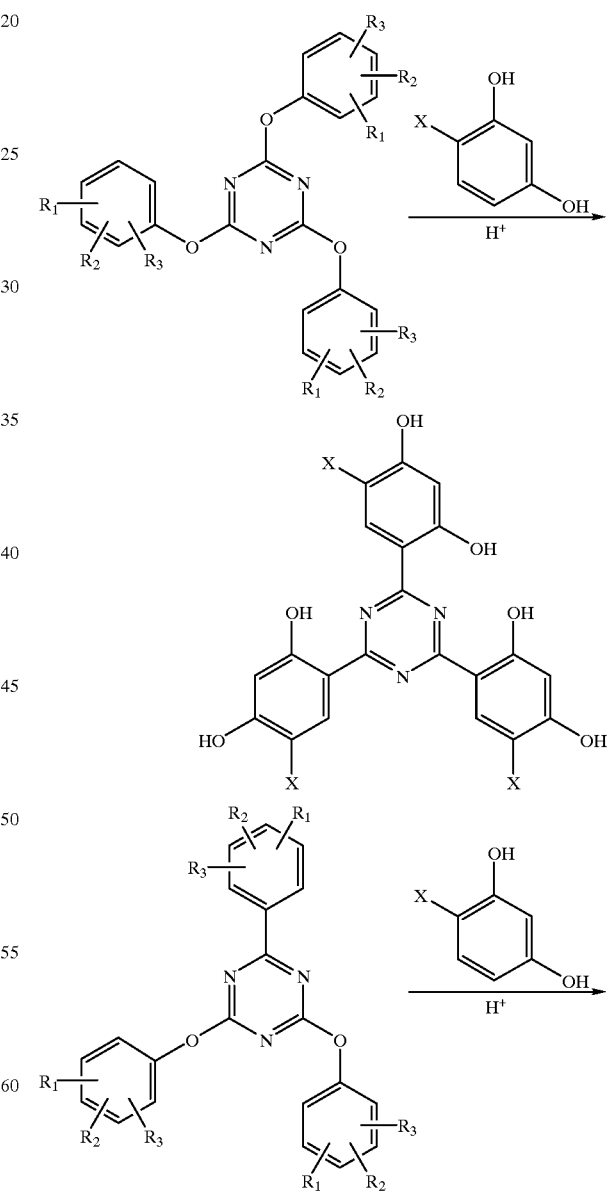

-continued

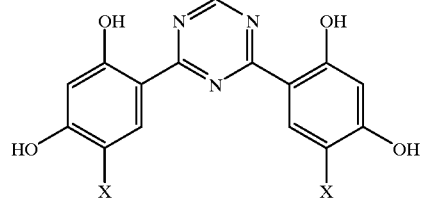

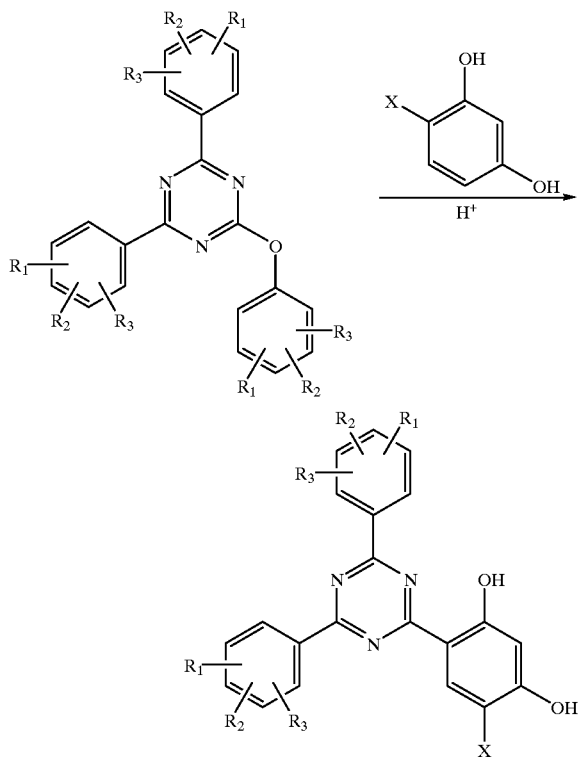

$R_1$, $R_2$ and $R_3$ are as defined above. The solvents and temperature ranges used are as above using chlorine as the leaving group.

The instant process also pertains to the preparation of asymmetric tris-aryl-s-triazines in only three steps while avoiding the selectivity problem of Friedel-Crafts reactions with cyanuric chloride. U.S. Pat. Nos. 5,084,570 and 5,106,972 describe a four-step process to overcome this selectivity problem. The key to the new three step process is to take advantage of a nucleophilic substitution step on cyanuric chloride which is selective (E. M. Smolin et al., loc cit). The nucleophile introduced into the triazine ring will also perform as a leaving group under Friedel-Crafts conditions. It is a poor leaving group compared to chlorine. In this way selectivity under Friedel-Crafts condition is achieved This allows one to avoid having to rechlorinate the triazine ring prior to subsequent Friedel-Crafts reactions thus reducing the number of synthetic steps. Effective nucleophiles which also serve as Friedel-Crafts leaving groups are alkoxy and aryloxy groups. Especially effective are phenoxy and substituted phenoxy.

For example, in order to prepare a mono-resorcinol-bis-aryl-s-triazine, cyanuric chloride is reacted with one mole of phenol or substituted phenol under nucleophilic (basic) conditions.

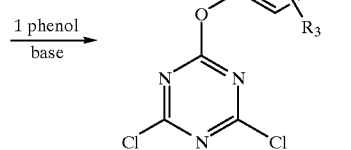

$R_1$, $R_2$ and $R_3$ are defined as above.

As mentioned above, the phenoxy group is an active Friedel-Crafts leaving group. It is a weaker one than chlorine thus allowing for the introduction of a relatively weak Friedel-Crafts substrate such as m-xylene, toluene, benzene, chlorobenzene or biphenyl while leaving the phenol group intact.

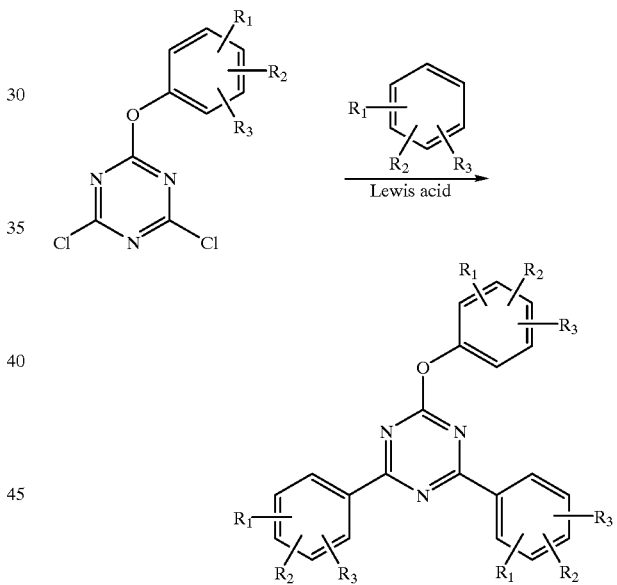

In the third step, the phenoxide may be replaced with a strong Friedel-Crafts substrate such as resorcinol.

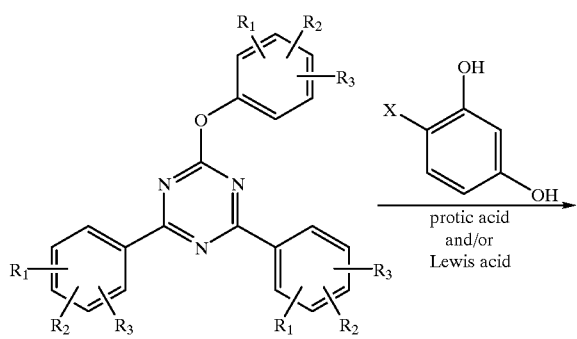

-continued

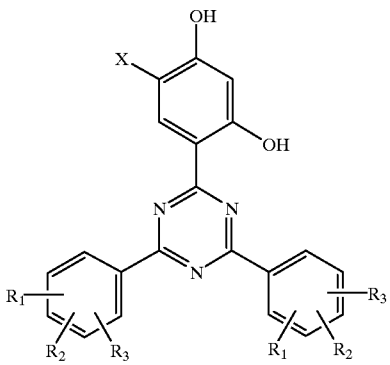

-continued

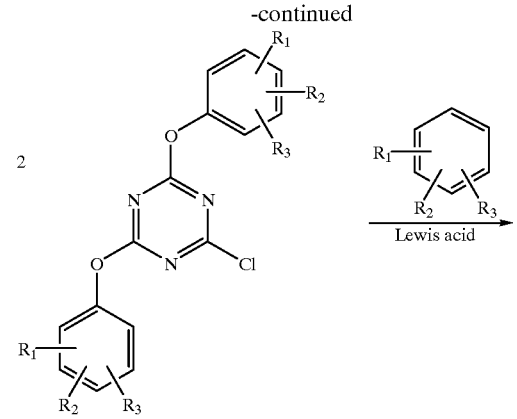

X, R₁, R₂ and R₃ are as defined above.

Japanese Hei 9-59263 discloses this three-step synthetic approach for the preparation of asymmetric tris-aryl-hydroxyphenyl-s-triazines. The preferred method of the Japanese reference is a one-pot process using a Lewis acid to mediate all three steps. The Japanese reference does not describe that step 3 can be mediated successfully by protic acids and that resorcinol itself may be used as a blocking group as is discussed further infra. This reference does not suggest the general applicability of the three-step synthesis. For example, the Japanese reference does not disclose that, if a Lewis acid is used for step 3, levels below 0.5 mol percent may be effective depending on reaction conditions. In reality, levels below 0.5 mol percent may be used to afford good yields of desired s-triazines.

Likewise, asymmetric tris-aryl-s-triazines which contain one weak and two strong Friedel-Crafts substrates may be prepared in three steps from cyanuric chloride. Examples are bis-resorcinol-mono-aryl-s-triazines where the aryl group is m-xylene, toluene, benzene, chlorobenzene or biphenyl. These materials are prepared by reacting cyanuric chloride with two moles of a phenol or substituted phenol under basic conditions to form a mono-chloro-bis-phenoxy-s-triazine. The remaining chlorine atom may be replaced with a weak Friedel-Crafts substrate such as m-xylene, toluene, benzene, chlorobenzene or biphenyl leaving the phenoxy groups intact. The phenoxy groups may then be replaced by a strong Friedel-Crafts substrate such as resorcinol.

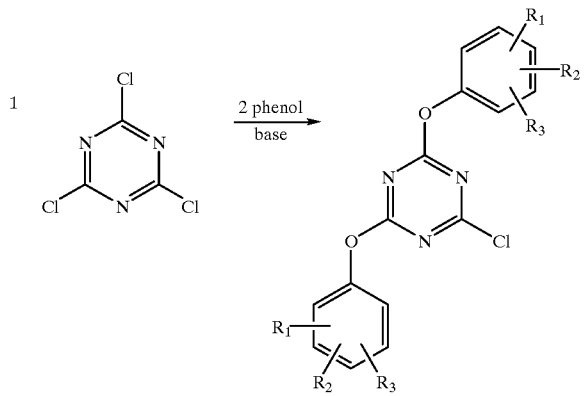

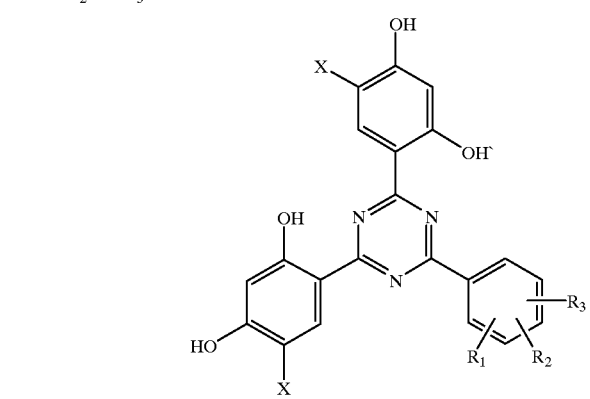

A special embodiment of this approach to prepare mono-resorcinol-bis-aryl-s-triazine would be to use resorcinol itself as the blocking phenol in step 1. A bis-triazine-resorcinol adduct is formed and is carried through steps 2 and 3 as seen above. This method is especially advantageous if excess resorcinol is used. In an industrial process only one phenol (namely resorcinol) would need to be recovered and recycled instead of two thus allowing for substantial cost savings. This embodiment is outlined below.

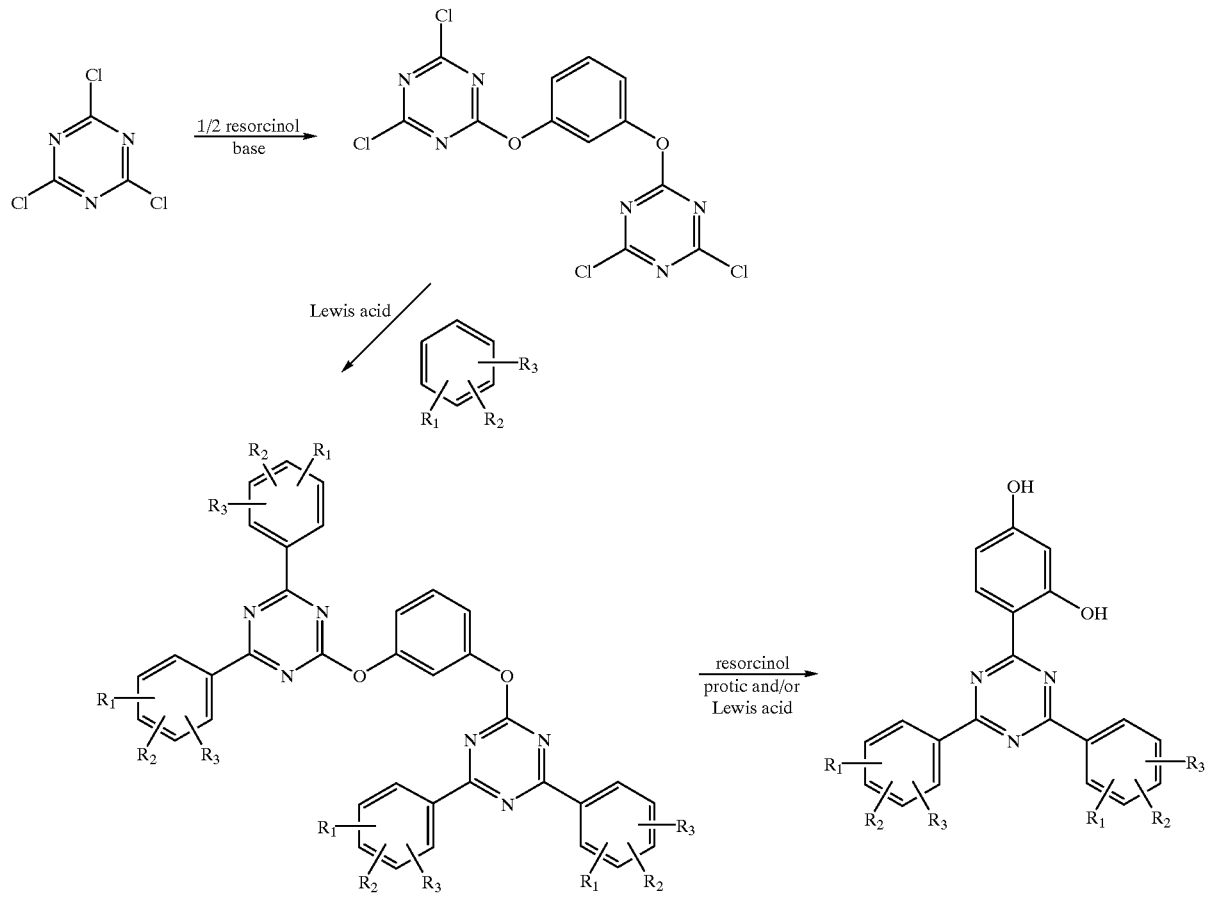

The nucleophilic first step in the special embodiment above may be performed in a variety of solvents such as acetone, acetone/water mixtures and xylene. It may also be carried out by means of a two-phase reaction with water and a hydrocarbon solvent such as xylene. A phase-transfer catalyst including quaternary ammonium salts or polyether such as glymes or poly(ethylene glycol) aids the reaction. Bases which can be used include hydroxide, carbonate and bicarbonate salts of sodium, potassium and calcium. Effective temperatures range from −20° C. to 100° C. The most effective temperatures range from −20° C. to 50° C.

Especially effective condition are the use of 10% water in acetone as solvent and sodium hydroxide as the base at a temperature range of −20° C. to 5° C. Also especially effective is the use of a two-phase system of water/xylene with sodium bicarbonate as the base and a quaternary ammonium salt such as benzyltrimethylammonium chloride as phase-transfer catalyst at temperatures of −5° C. to 10° C. Also especially effective is the use of benzyltrimethylammonium chloride as a catalyst in xylene at temperatures of −10° C. to 10° C. with potassium carbonate base under anhydrous conditions.

The second step in which chlorine is displaced by the weaker Friedel-Crafts substrate requires a Lewis acid catalyst. Aluminum chloride is the Lewis acid of choice and may be used in the range of 0.2 to 1.5 equivalents per equivalent of s-triazine. The reaction may be performed in a solvent such as chlorobenzene, dichlorobenzene or nitrobenzene, but is best performed neat using an excess of the Friedel-Crafts substrate as solvent. Effective amounts of neat Friedel-Crafts reactant range from 2 to 20 molar equivalents. Examples of solvents which may be employed in this way include m-xylene, toluene, benzene, chlorobenzene and biphenyl. An effective temperature range for this reaction is from 0° C. to 170° C.; especially from 70° C. to 150° C.

It is especially effective to perform the first step in a hydrocarbon solvent which will also be the Friedel-Crafts reactant for step two. Step two may then be performed without isolation of the product of step one.

Step three, in which the phenol is replaced by a strong Friedel-Crafts substrate such as resorcinol, may be performed with a protic acid or a Lewis acid catalyst or a combination of both protic acid and Lewis acid catalysts. The preferred protic acids are hydrogen chloride gas and methanesulfonic acid. A solvent may be used or the reaction may be performed in the neat molten resorcinol. Solvent choice may range from polar solvents such as tetramethylene sulfone to non-polar hydrocarbons such as m-xylene. Very often a single solvent may be used for all three steps. The amount of resorcinol may range from 1.2 to 10 molar equivalents per phenoxy group being displaced. The most effective range is from 1.2 to 4 molar equivalents of resorcinol per phenoxy moiety. The reaction may be performed with a catalyst level of 0.33 to 1.5 molar equivalents per triazine. The temperature for the reaction may range from 25° C. to 200° C. The most effective temperature range is from 120° C. to 170° C.

More specifically, there are six instant processes (A, B, C, D, E and F) as follows:

A is a process for preparing a compound of formula I (I)

[structure: X-substituted resorcinol linked to triazine with two aryl groups bearing R1, R2, R3]

where

X is hydrogen, alkyl of 1 to 12 carbon atoms, phenylalkyl of 7 to 15 carbon atoms or halogen, and $R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen, which process comprises (1). reacting cyanuric chloride

[structure: 2,4,6-trichloro-1,3,5-triazine]

with a phenolic compound of formula II (II)

[structure: phenol with R1, R2, R3 substituents]

to form a compound of formula III (III)

[structure: aryloxy-dichlorotriazine]

(2). reacting the compound of formula III with an aromatic hydrocarbon of formula IV (IV)

[structure: benzene with R1, R2, R3 substituents]

in the presence of an effective amount of a Lewis acid catalyst to give a compound of formula V (V)

[structure: aryloxy-diaryl triazine]

(3). reacting the compound of formula V with a compound of formula VI (VI)

[structure: X-substituted resorcinol]

in the presence of an effective amount of a protic acid or Lewis acid catalyst or a combination of a protic acid and Lewis acid catalysts to give the compound of formula I.

B is a process for preparing a compound of formula I (I)

[structure: same as formula I above]

where

X is hydrogen, alkyl of 1 to 12 carbon atoms, phenylalkyl of 7 to 15 carbon atoms or halogen, and $R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen, which process comprises (1). reacting cyanuric chloride

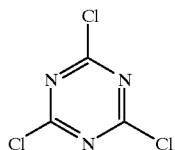

with a half equivalent of a resorcinol to form a compound of formula X (X)

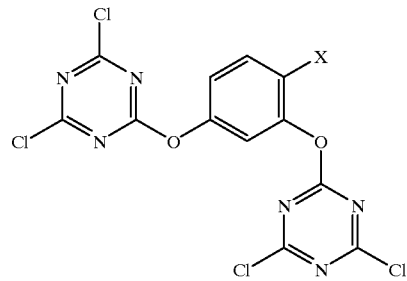

(2). reacting the compound of formula X with an aromatic hydrocarbon of formula IV (IV)

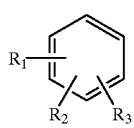

in the presence of an effective amount of a Lewis acid catalyst to give a compound of formula XI (XI)

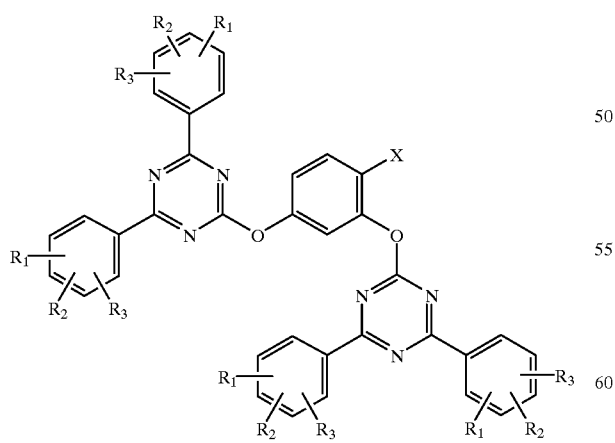

(3). reacting the compound of formula XI with a compound of formula VI (VI)

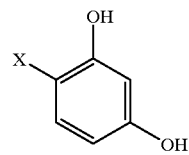

in the presence of an effective amount of a protic acid or Lewis acid catalyst or a combination of a protic acid and Lewis acid catalysts to give the compound of formula I.

C is a process for preparing a compound of formula VII (VII)

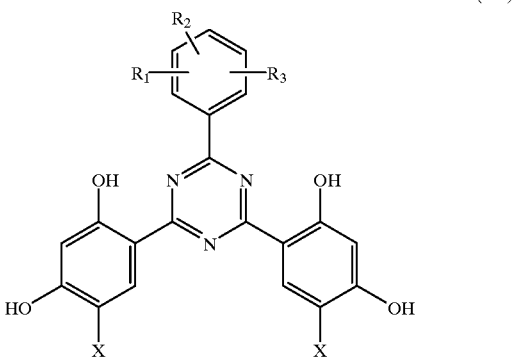

where

X is hydrogen, alkyl of 1 to 12 carbon atoms, phenylalkyl of 7 to 15 carbon atoms or halogen, and $R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen, which process comprises (1). reacting cyanuric chloride

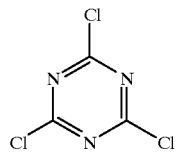

with two equivalents of a phenolic compound of formula II (II)

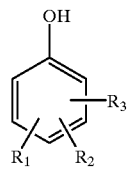

to form a compound of formula VIII

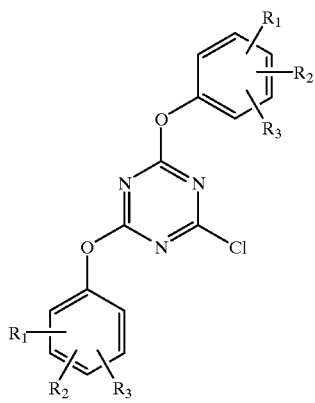
(VIII)

(2). reacting the compound of formula VIII with an aromatic hydrocarbon of formula IV

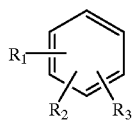
(IV)

in the presence of an effective amount of a Lewis acid catalyst to give a compound of formula IX

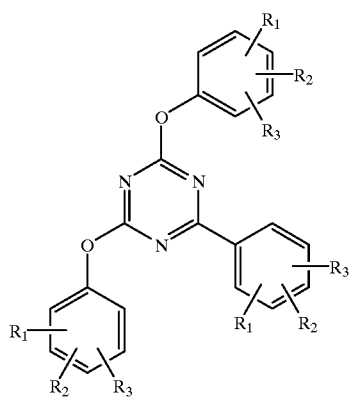
(IX)

(3). reacting the compound of formula IX with a compound of formula VI

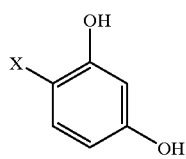
(VI)

in the presence of an effective amount of a protic acid or Lewis acid catalyst or a combination of a protic acid and Lewis acid catalysts to give the compound of formula VII.

In the processes A, B and C, step 1 is carried out in the presence of a base or Lewis acid, which is preferably aluminum chloride.

When in processes A, B and C, step 1 is carried out in the presence of a base, said base is preferably a hydroxide, carbonate or bicarbonate of sodium, potassium or calcium. Most preferably sodium hydroxide, sodium bicarbonate or potassium carbonate.

In processes A, B and C, step 1 is preferably run in acetone, acetone/water or a hydrocarbon. Another embodiment is when step 1 is run in a two-phase system of water and a hydrocarbon solvent, preferably xylene and where the phase transfer agent is a quaternary ammonium salt, a polyether or a poly(ethylene glycol), most preferably a quaternary ammonium salt, which is benzyltrimethylammonium chloride. Another embodiment is when step 1 is run in xylene with a phase transfer catalyst and potassium carbonate base under anhydrous conditions.

In processes A and B, step 1 is run at −20° C. to 100° C.; preferably at −20° C. to 50° C.

In process C, step 1 is run at −20° C. to 200° C.; preferably at −20° C. to 130° C.

In processes A and B, step 1 is preferably run in 10% water in acetone with sodium hydroxide as base at a temperature of −20° C. to 5° C.

In process C, step 1 is preferably run in 10% water in acetone with sodium hydroxide as base at a temperature of −20° C. to 60° C.

In another embodiment of processes A and B, step 1 is run in a two-phase system of aromatic hydrocarbon/water with sodium bicarbonate as the base and benzyltrimethylammonium chloride as a phase transfer catalyst at a temperature of −5° C. to 10° C.

In another embodiment of process C, step 1 is run in a two-phase system of aromatic hydrocarbon/water with sodium bicarbonate as the base and benzyltrimethylammonium chloride as phase transfer catalyst at a temperature of −5° C. to 110° C.

In still another embodiment of processes A and B, step 1 is run in xylene with benzyltrimethylammonium chloride as catalyst and potassium carbonate as base under anhydrous conditions at a temperature of −10° C. to 10° C.

In another embodiment of process C, step 1 is run in xylene with benzyltrimethylammonium chloride as catalyst and potassium carbonate as base under anhydrous conditions at a temperature of −10° C. to 110° C.

Still another embodiment of processes A, B and C, the product of step 1 is not isolated.

In processes A, B and C, in step 2 the Lewis acid is aluminum chloride, preferably wherein the aluminum chloride is used in the range of 0.2 to 1.5 equivalents per one equivalent of s-triazine.

In processes A, B and C, step 2 is run at a temperature of 0° C. to 170° C.; especially 70° C. to 150° C.

In processes A, B and C, step 2 is run neat in an excess of aromatic compound of formula IV, preferably where the aromatic compound of formula IV is m-xylene, toluene, benzene, chlorobenzene or biphenyl.

In processes A, B and C, the compound of formula IV is used in the range of from 2 to 20 molar equivalents per equivalent of triazine of the compound of formula III, X or VIII.

In processes A, B and C, III, X or VIII are not isolated, the Lewis acid is added and the temperature increased, if necessary, to produce the compound of formula V, XI or IX.

In processes A, B and C, in step 3 a protic acid is used which is preferably hydrogen chloride gas or methanesulfonic acid.

In processes A, B and C, in step 3, 1.2 to ten equivalents of resorcinol are used per each phenoxy-triazine bond.

In processes A, B and C, step 3 is carried out at a temperature of from 25° C. to 200° C., preferably from 120° C. to 170° C.

In processes A, B and C, in step 3, four equivalents of resorcinol and 1 to 1.5 equivalents of methanesulfonic acid are used per each phenoxy-triazine bond; or four to ten equivalents of resorcinol and 0.20 to 0.49 equivalents of Lewis acid are used per each phenoxy-triazine bond; or 1.2 to 1.5 equivalents of resorcinol and 0.8 to 1.5 equivalents of Lewis acid are used per each phenoxy-triazine bond.

In processes A, B and C, step 3 may be performed neat or the aromatic compound IV used in step 2 may be the solvent or the solvent may be tetramethylene sulfone.

D is a process for preparing a compound of formula XII

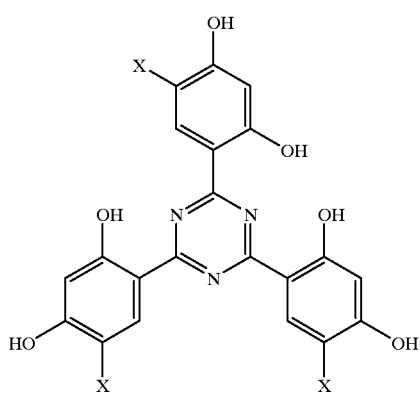
(XII)

where

X is hydrogen, alkyl of 1 to 12 carbon atoms, phenylalkyl of 7 to 15 carbon atoms or halogen, which process comprises reacting cyanuric chloride

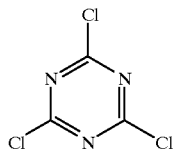

with a resorcinol of formula VI

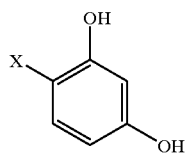
(VI)

in the presence of an effective amount of a protic acid to form a compound of formula XII.

E is a process for the preparing a compound of formula I

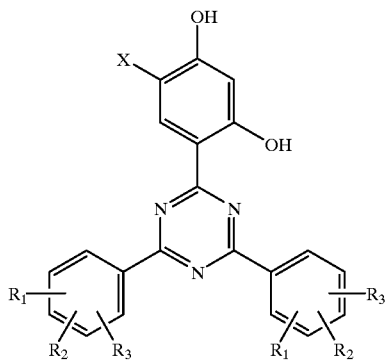
(I)

where

X is hydrogen, alkyl of 1 to 12 carbon atoms, phenylalkyl of 7 to 15 carbon atoms or halogen, and $R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen, which process comprises reacting a compound of formula XIII

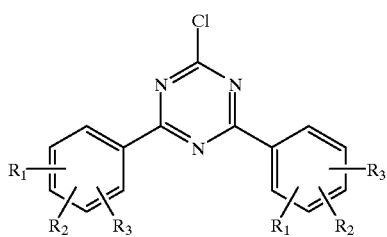
(XIII)

with a compound of formula VI

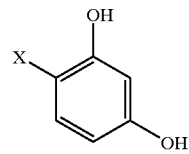
(VI)

in the presence of an effective amount of a protic acid to form a compound of formula I.

F is a process for the preparing a compound of formula XII

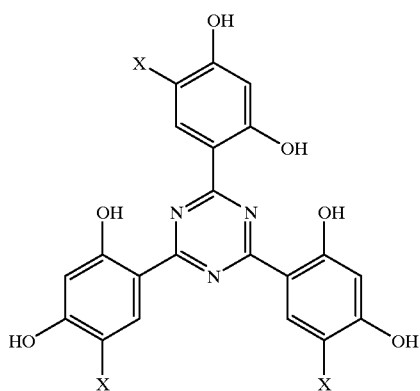

(XII)

where

X is hydrogen, alkyl of 1 to 12 carbon atoms, phenylalkyl of 7 to 15 carbon atoms or halogen, which comprises reacting a compound of formula XV

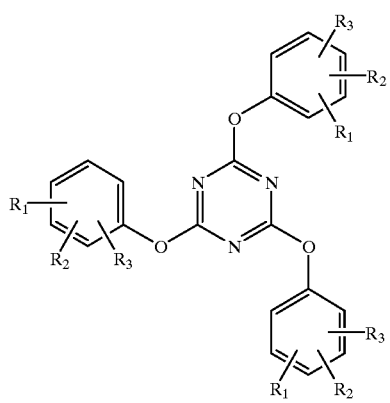

(XV)

where $R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen, with a compound of formula (VI)

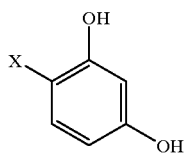

(VI)

in the presence of an effective amount of a protic acid to form a compound of formula XII.

In processes D, E and F, the reaction is carried out in the melt or in a solvent where the solvent is an aromatic hydrocarbon or tetramethylene sulfone.

In processes D and E, no catalyst is used and 1.2 to ten equivalents of resorcinol are used per equivalent of chloride.

In processes D, E and F, a protic acid catalyst is used which is hydrogen chloride or methanesulfonic acid.

In processes D, E and F, a protic acid catalyst is used along with a Lewis acid potentiator at a level of less than 0.25 equivalents of Lewis acid per equivalent of chloride or phenol.

In processes D, E and F, the reaction is carried out at a temperature of −30° C. to 250° C.; preferably from 70° C. to 200° C.; and most preferably at 100° C. to 170° C.

The following examples are meant for illustrative purposes only and are not to be construed to limit the scope of the instant invention in any manner whatsoever.

EXAMPLE 1

2,4,6-Tris-(2,4-dihydroxyphenyl-s-triazine

To a 250 mL round-bottomed flask equipped with a condenser, magnetic stirrer and a nitrogen atmosphere is charged 5.60 g (0.0510 mol) of resorcinol. The stirred resorcinol is heated to 120° C. at which point it becomes molten. A 2.08 g (0.0113 mol) portion of cyanuric chloride is added all at once resulting in an immediate evolution of hydrogen chloride gas. After 30 minutes, a portion of water is added and the mixture is refluxed for two hours and then allowed to cool to room temperature. The crude yellow powder (3.52 g) is collected by vacuum filtration. $^1$H nmr (DMSO-$d_6$) reveals an overall conversion of 50% to the title compound.

Alternatively:

To a 250 mL round-bottomed flask equipped with a condenser, magnetic stirrer anda nitrogen atmosphere is added 1.00 g(2.80 mmol)of cyanuric chloride, 5.00 g (45.5 mmol) of resorcinol and 0.21 g (2.2 mmol) of methanesulfonic acid. The molten mixture is stirred at 130° C. for 2.5 hours. The mixture is then triturated with hot water and 0.410 g of a brown-red solid is collected by vacuum filtration. $^1$H nmr (DMSO-$d_6$) reveals the presence of the title compound.

EXAMPLE 2

4,6-Bis-(2,4-dimethylphenyl)-2-phenoxy-s-triazine

To a 1 L four-necked, round-bottomed flask equipped with a mechanical stirrer and an addition funnel is charges 37.5 g (0.203 mol) of cyanuric chloride and 200 mL of m-xylene. The suspension/solution is chilled below 5° C. and 34.5 g of sodium bicarbonate, 200 mL of water and 1.4 g of benzyltrimethylammonium chloride are added. The contents of the flask are again cooled below 5° C. A solution of phenol (19.2 g, 0.203 mol) in 100 mL of m-xylene is charged to the addition funnel and then added over a 10-minute period to the reaction flask while the temperature is maintained between 1° C. and 3° C. The mixture is then stirred at 2–7° C. for five hours.

The mixture is then warmed to 50° C. and the phases are separated. The organic phases is returned to the reaction flask and 32.5 g (0.244 mol) of aluminum chloride are added at 35° C. The mixture is then heated at about 130° C. for three hours. The contents are cooled below 120° C. and poured into 500 mL of cold 2N hydrochloric acid. The phases are separated and the organic phases is washed twice with water and one with saturated sodium bicarbonate solution. After drying over anhydrous potassium carbonate, the solvent is removed under reduced pressure to afford an oil which crystallized upon cooling. The crude solid is recrystallized from isopropanol to afford 57.7 g (75% yield) of the title compounds melting at 96–98° C.

Examples 3–8, 10 and 13 below represent some of the various novel methods which can be used to prepare 4,6-bis-(2,4-dimethylphenyl)-2-(2,4-dihydroxyphenyl)-s-triazine.

EXAMPLE 3

4,6-Bis-(2,4-dimethylphenyl)-2-(2,4-dihydroxyphenyl)-s-triazine

To a 50 mL round-bottomed flask equipped with a magnetic stirrer, condenser and nitrogen atmosphere are charged 1.00 g (3.10 mmol) of 4,6-bis-(2,4-dimethylphenyl)-2-chloro-s-triazine and 1.70 g (15.5 mmol) of resorcinol. The mixture is stirred at 180° C. for five hours at which point $^1$H nmr (CDCl$_3$) of an aliquot reveals a 72% overall conversion to the title compound.

EXAMPLE 4

4,6-Bis-(2,4-dimethylphenyl)-2-(2,4-dihydroxyphenyl)-s-triazine

To a 500 mL four-necked, round-bottomed flask fitted with a mechanical stirrer, a nitrogen atmosphere and an oil bath are added 20.0 g (0.0524 mol) of the product of Example 2, 23.0 g (0.209 mol) of resorcinol. 7.6 g (0.079 mol) of methanesulfonic acid and 25 mL of m-xylene. The mixture is stirred at 120° C. for 20 hours and then allowed to cool to room temperature. A 200 mL portion of heptane and 200 g of ice are added. The contents are warmed to 55° C. and then allowed to cool to below 40° C. The crude solid formed is isolated by filtration, washed with water and heptane and then dried under reduced pressure to yield 17.5 g of yellow-orange crude product. The material is ground in a mortar, taken up in 170 mL of methanol, cooled to −20° C. and then filtered to afford 12.8 g (62% yield) of the title compound as a yellow solid melting at 203–205° C.

EXAMPLE 5

4,6-Bis-(2,4-dimethylphenyl)-2-(2,4-dihydroxyphenyl)-s-triazine

To a 250 mL round-bottomed flask fitted with a magnetic stirrer, a condenser and a nitrogen atmosphere are charged 6.26 g (0.0164 mol) of the product of Example 2, 12.8 g (0.116 mol) of resorcinol, 2,4 g of NAFION® NR50 beads 10–35 and 2 mL of xylene. The mixture is heated to 160° C. for 8.5 hours and then allowed to cool to room temperature. A 2.13 g (0.0160 mol) of aluminum chloride is added all at once. The mixture is then heated to 160° C. for two hours. An aliquot is worked up by adding portions of 2N hydrochloric acid and heptane and collecting the solid by vacuum filtration. $^1$H nmr (CDCl$_3$) reveals a complete conversion to the title compound.

EXAMPLE 6

4,6-Bis-(2,4-dimethylphenyl)-2-(2,4-dihydroxyphenyl)-s-triazine

To a 250 mL round-bottomed flask fitted with a magnetic stirrer, a condenser and a nitrogen atmosphere are charged 7.85 g (0.0206 mol) of the product of Example 2, 13.5 g (0.123 mol) of resorcinol, 4 mL of m-xylene and 0.954 g (7.16 mmol) of aluminum chloride. The mixture is heated to 150° C. for 13.5 hours and then allowed to cool to 90° C. Portions of 2N hydrochloric acid and heptane are added and the mixture is stirred at 90° C. for 30 minutes followed by stirring for 18 hours at room temperature. The mixture is then warmed to 35° C. The crude solid formed is collected by vacuum filtration and is washed with portions of water and heptane. The solid is then recrystallized twice from methanol to afford 4.76 g (62% yield) of the title compound as a yellow solid melting at 194–196° C.

EXAMPLE 7

4,6-Bis-(2,4-dimethylphenyl)-2-(2,4-dihydroxyphenyl)-s-triazine

To a 250 mL round-bottomed flask equipped with a magnetic stirrer, a condenser and a nitrogen atmosphere are added 6.00 g (0.0157 mol) of the product of Example 2, 2.08 g (0.0189 mol) of resorcinol, 2.09 g (0.0157 mol) of aluminum chloride and 6 mL of tetramethylene sulfone (sulfolane). The mixture is stirred at 138° C. for six hours, 147° C. for seven hours, 160° C. for 10.5 hours and then allowed to cool to room temperature. A portion of 2N hydrochloric acid is added and the mixture is refluxed for two hours and then allowed to cool to room temperature. The solids formed are collected by vacuum filtration and then washed with portions of water and heptane. The crude solid is taken up in ethyl acetate and passed through a plug of silica gel. The solvent is removed under reduced pressure to give 5.25 g of crude product. The crude product is recrystallized from methanol to afford 4.29 g (69% yield) of the title compound as a yellow solid melting at 199–201° C.

EXAMPLE 8

4,6-Bis-(2,4-dimethylphenyl)-2-(2,4-dihydroxyphenyl)-s-triazine

A 300 mL three-necked, round-bottomed flask fitted with a magnetic stirrer, an acid trap, a gas inlet and a heat lamp to prevent sublimation is charged with 29.9 g (0.272 mol) of resorcinol and 2.00 g (0.00525 mol) of the product of Example 2. The mixture is heated to 150° C. and hydrogen chloride gas is bubbled slowly through the molten mixture for 25 minutes. The mixture is stirred at this temperature for another 4.5 hours and then allowed to cool to room temperature. Portions of water and toluene are added and the mixture is refluxed till the solids are dissolved. The mixture is allowed to cool to room temperature and the layers separated. The organic layer is washed once with water, twice with saturated sodium bicarbonate solution and once with brine. After drying over anhydrous magnesium sulfate and filtering, the solvent is removed under reduced pressure to afford 1.56 g of crude product. Purification by flash chromatography on silica gel with 3:1 heptane:ethyl acetate gives 1.19 g (57% yield) of the title compound as a yellow solid.

EXAMPLE 9

2,4-Bis-(2,4-dimethylphenyl)-2-(n-propoxy)-s-triazine

A 500 mL round-bottomed flask fitted with a condenser, a magnetic stirrer and a nitrogen atmosphere is charged with 5.48 g (0.0169 mol) of 4,6-bis-(2,4-dimethylphenyl-2-chloro-s-triazine, 10.2 g (0.169 mol) of n-propanol, 2,37 g (0.0246 mol) of methane-sulfonic acid and 25 mL of m-xylene. The mixture is stirred at 90° C. for one hour. The mixture is then allowed to cool to room temperature and vacuum filtered through a plug of silica gel which is subsequently washed with 95:5 heptane:ethyl acetate. The combined organic layers are vacuum filtered through another plug of silica gel. The solvent is removed under reduced pressure to afford 3.31 g of the title compound as off-white crystals melting at 86–88° C.

EXAMPLE 10

4,6-Bis-(2,4-dimethylphenyl)-2-(2,4-dihydroxyphenyl)-s-triazine

To a 250 mL round-bottomed flask fitted with a condenser, magnetic stirrer and a nitrogen atmosphere are added 1.44 g (4.16 mmol) of the product of Example 9, 1.98 g (0.0180 mol) of resorcinol, 0.59 g (6.2 mmol) of methanesulfonic acid and 2.7 mL of m-xylene. The mixture is stirred at 125° C. for one hour and then refluxed for an additional five hours. The mixture is allowed to cool to room temperature and portions of heptane and water are added. The gooey mixture is encouraged to form solids by scratching with a glass rod. The solids formed are collected by vacuum filtration and dried to give 1.04 g of a red-brown solid. $^1$H nmr (CDCl$_3$) reveals that the title compound makes up approximately 15 molar percent of the recovered solid.

EXAMPLE 11

1,3-Bis-(2,4-dichloro-s-triazinoxy)benzene

A 1 L jacketed reaction flask equipped with a gas inlet, a mechanical stirrer, two liquid inlets and a condenser is purged with argon and charged with 37.3 g (0.0200 mol) of cyanuric chloride and 300 mL of acetone. The stirred mixture is cooled below −15° C. and 30 mL of deionized water are added. A 10% aqueous sodium hydroxide solution (88 g) are added over a 66-minute period via a peristaltic pump. Six minutes after the sodium hydroxide addition is started, a resorcinol solution (11.0 g, 0.100 mol in 50 mL of water) addition is begun also via a peristaltic pump. The resorcinol solution is then added over a 60-minute period concurrent with the sodium hydroxide solution. A slight exotherm occurs causing the temperature to rise to −12° C. The mixture is then stirred for an additional four hours at between −15° C. and −20° C. A 200 mL poriton of water is added and the white solids formed are collected by vacuum filtration followed by washing with three 50 mL portions of water. The solids are dried at 60° C. under reduced pressure to afford 36.5 g of the title compound as a white solid.

EXAMPLE 12

1,3-Bis-(4,6-bis-(2,4-dimethylphenyl)-s-triazinoxy) benzene

To a 500 mL round-bottomed flask fitted with a magnetic stirrer, a condenser and a nitrogen atmosphere are added 2.33 g (5.74 mmol) of the product of Example 11 and 25 mL of m-xylene. The mixture is stirred with warming and, when it becomes homogeneous at about 40° C., 1.84 g (0.0138 mol) of aluminum chloride are added all at once. The mixture is brought to reflux and stirred at this temperature for three hours. After cooling to room temperature, a 100 mL portion of 2N hydrochloric acid is added. The mixture is heated with stirring for 15 minutes and allowed to cool. Portions of ethyl acetate and heptane are added and the solids formed are collected by vacuum filtration. The solids are washed with ethyl acetate and water, then dried to afford 2.58 g of the title compound as an off-white solid.

EXAMPLE 13

4,6-Bis-(2,4-dimethylphenyl)-2-(2,4-dihydroxyphenyl)-s-triazine

A 350 mL Paar reaction vessel equipped with a magnetic stirrer is charged with 4.12 g (6.02 mmol) of the product of Example 12, 7.00 g (0.0636 mol) of resorcinol and 4.3 mL of m-xylene. The vessel is connected to a hydrogen chloride lecture bottle via TEFLON® (duPont) tubing and the system includes a MONEL® (Inco Alloys) gauge and MONEL® valves. The system is flushed once with hydrogen chloride and is brought to a pressure of 5.5 lb/in$^2$ of hydrogen chloride. The system is brought to an external temperature of 170° C. and the pressure increases to 14.5 lb/in$^2$. The mixture is stirred at this temperature for eight hours and at an external temperature of 160° C. for an additional 17 hours. The mixture is allowed to cool to room temperature and portions of water and heptane are added. The mixture is stirred with warming and allowed to cool. The solids formed are collected by vacuum filtration to afford 5.10 g of crude product as a yellow-brown powder. The crude product is recrystallized from methanol to give 1.92 g of the title compound as a yellow solid.

EXAMPLE 14

4,6-Diphenyl-2-(2,4-dihydroxyphenyl)-s-triazine

A 500 mL three-necked, round-bottomed flask equipped with a mechanical stirrer is charged with 60 g of xylene and 55.5 g (0.207) of 4,6-diphenyl-2-chloro-s-triazine. The mixture is warmed to 118° C. and the pressure is reduced to 300 mbar and 2.8 g of hydrogen chloride gas is charged to the system. The mixture is cooled to 80° C. and a solution of resorcinol (88.2 g, 0.802 mol) in 60 g of tetramethylene sulfone is added dropwise over a 7-minute period. The mixture is stirred at 80° C. for six hours and then for one hour at 100° C. The temperature is reduced to 60° C. and a 300 mL portion of methanol is added. The mixture is allowed to cool to room temperature and is stirred overnight. Sodium methoxide (41.3 g) is added portionwise to adjust the pH to 5.0–5.5. The solids are collected by vacuum filtration and are washed with methanol and water. After drying, the title compound is obtained in a yield of 59.2 g as a pale yellow solid.

EXAMPLE 15

2-Chloro-4,6-diphenoxy-s-triazine

A 2-liter reaction flask equipped with a magnetic stirrer and a condenser is charged with 92.2 g (0.50 mol) of cyanuric chloride, 84 g (1.0 mol) of sodium bicarbonate and 400 mL of toluene. The suspension is brought to 50° C. and 94 g (1.0 mol) of phenol are added in small portions. The mixture is refluxed for ten hours and then allowed to cool to room temperature. Portions of water and ethyl acetate (300 mL each) are added and the mixture is then filtered. The phases are separated and the organic phase is dried over anhydrous magnesium sulfate. The solvent is removed under reduced pressure to afford 150 g of crude product. The crude product is twice recrystallized from toluene to yield 48.7 g of the title compound as a white powder melting at 117–121° C.

EXAMPLE 16

2,4-Diphenoxy-6-(2,4,6-trimethylphenyl)-s-triazine

A 250-mL reaction flask fitted with a magnetic stirrer and a condenser is charged with 21.0 g (0.070 mol) of the product of Example 15, 100 mL of mesitylene and 9.30 g (0.070 mol) of aluminum chloride. The mixture is refluxed for three days. The mixture is then poured onto ice and the phases are separated. The organic phase is dried over anhydrous sodium sulfate and the solvent is removed under reduced pressure to give a brown resin. The crude resin is recrystallized from ligroin to give 7.9 g of the title compound as a white powder melting at 135–143° C.

EXAMPLE 17

2,4-Bis-(2,4-dihydroxyphenyl)-6-(2,4,6-trimethylphenyl)-s-triazine

A 100 mL reaction flask is charged with 1.90 g (4.96 mmol) of the product of Example 16, 2.75 g (0.025 mol) of resorcinol, 0.72 g (7.5 mmol) of methanesulfonic acid and 20 mL of xylene. The mixture is heated for five hours at 125° C. and then cooled to 50° C. Portions of water and ethyl acetate (25 mL each) are added and the phases are separated. The organic phase is dried over anhydrous magnesium sulfate. The solvent is then removed under reduced pressure. The recovered residue is chromatographed on silica gel to afford 300 mg of the title compound as a yellow solid.

EXAMPLE 18

2,4-Bis-(2,4-dihydroxyphenyl)-6-phenyl-s-triazine

Following the procedure of Example 14, the title compound is prepared by the reaction of 2,4-dichloro-6-phenyl-s-triazine and resorcinol.

What is claimed is:

1. A process for preparing a compound of formula I

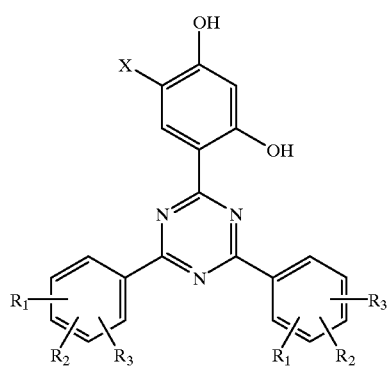

(I)

where

X is hydrogen, alkyl of 1 to 12 carbon atoms, phenylalkyl of 7 to 15 carbon atoms or halogen, and $R_1$, $R_2$ and $R_3$ are each independently hydrogen, alkyl of 1 to 12 carbon atoms, hydroxy, alkoxy of 1 to 12 carbon atoms, halogen, phenyl or phenyl substituted by alkyl of 1 to 12 carbon atoms, hydroxy, alkoxy of 1 to 12 carbon atoms or halogen, which process comprises (1). reacting cyanuric chloride

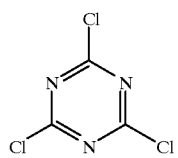

with a phenolic compound of formula II

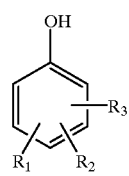

(II)

to form a compound of formula III

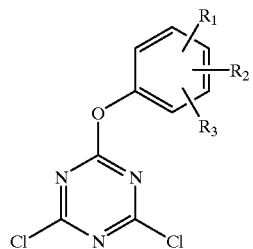

(III)

(2). reacting the compound of formula III with an aromatic hydrocarbon of formula

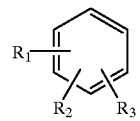

(IV)

in the presence of an effective amount of a Lewis acid catalyst to give a compound of formula V

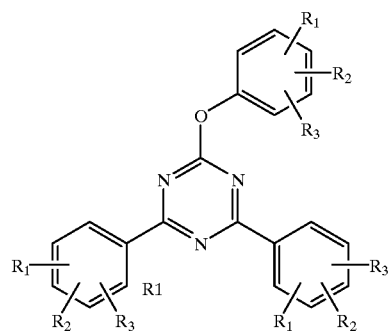

(V)

(3). reacting the compound of formula V with a compound of formula VI

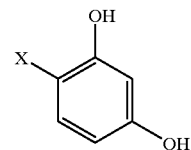

(VI)

in the presence of an effective amount of a protic acid catalyst or a Lewis acid catalyst or a combination of protic acid and Lewis acid catalysts to give the compound of formula I.

2. A process according to claim 1 wherein step 1 is carried out in the presence of a base or Lewis acid.

3. A process according to claim 2 wherein the Lewis acid is aluminum chloride.

4. A process according to claim 1 wherein step 1 is carried out in the presence of a base.

5. A process according to claim 4 wherein the base is a hydroxide, carbonate or bicarbonate of sodium, potassium or calcium.

6. A process according to claim 5 wherein the base is sodium hydroxide, sodium bicarbonate or potassium carbonate.

7. A process according to claim 1 wherein step 1 is run in acetone, acetone/water or a hydrocarbon.

8. A process according to claim 1 wherein step 1 is run in a two-phase system of water and a hydrocarbon solvent.

9. A process according to claim 8 wherein the hydrocarbon solvent is xylene.

10. A process according to claim 8 wherein a phase transfer agent is used which is a quaternary ammonium salt, a polyether or a poly(ethylene glycol).

11. A process according to claim 10 wherein the phase transfer agent is a quaternary ammonium salt.

12. A process according to claim 11 wherein the quaternary ammonium salt is benzyltrimethylammonium chloride.

13. A process according to claim 1 wherein step 1 is run at −20° C. to 100° C.

14. A process according to claim 13 wherein step 1 is run at −20° C. to 50° C.

15. A process according to claim 1 wherein step 1 is run in 10% water in acetone with sodium hydroxide as base at a temperature of −20° C. to 5° C.

16. A process according to claim 1 wherein step 1 is run in a two-phase system of aromatic hydrocarbon/water with sodium bicarbonate as the base and benzyltrimethylammonium chloride as a phase transfer catalyst at a temperature of −5° C. to 10° C.

17. A process according to claim 1 wherein step 1 is run in xylene with benzyltrimethylammonium chloride catalyst and potassium carbonate base under anhydrous conditions at −10° C. to 10° C.

18. A process according to claim 1 wherein the product of step 1 is not isolated.

19. A process according to claim 1 where in step 2 the Lewis acid is aluminum chloride.

20. A process according to claim 19 wherein the aluminum chloride is used in the range of 0.2 to 1.5 equivalents per one equivalent of s-triazine.

21. A process according to claim 1 wherein step 2 is run at a temperature of 0° C. to 170° C.

22. A process according to claim 21 wherein step 2 is run at a temperature of 70° C. to 150° C.

23. A process according to claim 1 wherein step 2 is run neat in an excess of aromatic compound of formula IV.

24. A process according to claim 23 wherein the aromatic compound of formula IV is m-xylene, toluene, benzene, chlorobenzene or biphenyl.

25. A process according to claim 23 wherein the compound of formula IV is used in the range of from 2 to 20 molar equivalents per equivalent of the compound of formula III.

26. A process according to claim 18 in which the product of step 1 is not isolated, the Lewis acid is added and the temperature increased, if necessary, to produce the compound of formula V.

27. A process according to claim 1 where in step 3 a protic acid catalyst is used.

28. A process according to claim 27 wherein the protic acid is hydrogen chloride gas.

29. A process according to claim 27 wherein the protic acid is methanesulfonic acid.

30. A process according to claim 1 where in step 3, 1.2 to ten equivalents of resorcinol are used per one equivalent of triazine.

31. A process according to claim 1 wherein step 3 is carried out at a temperature of from 25° C. to 200° C.

32. A process according to claim 31 wherein the temperature is from 120° C. to 170° C.

33. A process according to claim 1 where in step 3, four equivalents of resorcinol and 1 to 1.5 equivalents of methanesulfonic acid are used per one equivalent of triazine.

34. A process according to claim 1 where in step 3, four to ten equivalents of resorcinol and 0.20 to 0.49 equivalents of Lewis acid are used per one equivalent of triazine.

35. A process according to claim 1 where in step 3, 1.2 to 1.5 equivalents of resorcinol and 0.8 to 1.5 equivalents of Lewis acid are used per one equivalent of triazine.

36. A process according to claim 1 where step 3 is run neat.

37. A process according to claim 1 where in step 3, the solvent is the aromatic compound IV used in step 2.

38. A process according to claim 1 where in step 3, the solvent is tetramethylene sulfone.

* * * * *